United States Patent [19]

Carpenter et al.

[11] 4,289,140
[45] Sep. 15, 1981

[54] SIGNAL PROCESSING SYSTEM

[76] Inventors: David A. Carpenter, 44 Bellambi St.; George Kossoff, 38 Lower Cliff Ave., both of Northbridge, 2063, New South Wales; George D. Radovanovich, 4 Ethie Ave., Beacon Hill, 2100, New South Wales, all of Australia

[21] Appl. No.: 71,098
[22] Filed: Aug. 31, 1979

Related U.S. Application Data

[63] Continuation-in-part of Ser. No. 903,562, May 8, 1978, abandoned.

[30] Foreign Application Priority Data

May 6, 1977 [AU] Australia ............................ PD0005

[51] Int. Cl.³ .......................................... A61B 10/00
[52] U.S. Cl. .......................................... 128/660; 73/631
[58] Field of Search ............................ 128/660–663, 128/24 A; 328/145, 162–163; 307/230, 260, 263–264; 73/631

[56] References Cited

U.S. PATENT DOCUMENTS

| | | | |
|---|---|---|---|
| 3,458,652 | 7/1969 | McMann, Jr. | 328/163 |
| 3,483,475 | 12/1969 | Mitchell | 328/145 |
| 3,483,860 | 12/1969 | Nomerov | 128/663 |
| 3,509,368 | 4/1970 | Pederson | 328/145 |
| 3,636,462 | 1/1972 | Ougkiehong | 367/67 |
| 3,650,277 | 3/1972 | Sjostrand et al. | 128/421 |
| 3,793,480 | 2/1974 | Woebner | 307/230 |
| 3,813,609 | 5/1974 | Wilkes et al. | 367/67 |
| 3,919,657 | 11/1975 | Howlett et al. | 367/67 |
| 3,938,050 | 2/1976 | Corbett et al. | 328/127 |
| 4,016,862 | 4/1977 | Lancee et al. | 128/660 |
| 4,090,150 | 5/1978 | Vochenauer | 328/145 X |

*Primary Examiner*—Robert W. Michell
*Assistant Examiner*—Francis J. Jaworski

[57] ABSTRACT

Echoscopes incorporating signal processing circuits capable of providing a more complete and useful display of information received as a train of electrical signals. In one circuit, which is essentially a compression amplifier, the amplitude range of the input signal is limited by way of two or three amplitude limiting stages and an adder connected to sum the output of the first and last stages provides an advantageous output to input characteristic for the circuit.

The second circuit includes filter means and derivating means to separately process the input signal, and an adder to combine the outputs of these means to obtain a signal of enhanced utility.

5 Claims, 8 Drawing Figures

SIGNAL PROCESSING SYSTEM

CROSS REFERENCE

This application is a continuation-in-part of application Ser. No. 903,562 filed May 8, 1978 now abandoned.

This invention relates to novel electrical signal processing circuits having particular though by no means exclusive application to the technique of ultrasonic echoscopy of objects. In such application, the circuits are of assistance in providing a more complete and diagnostically useful display of the results of the examination of the objects.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1-30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed for example as a deflection of the base line "A mode" or as an intensity change "B mode". In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display, for example, as a deflection of the base line or as an intensity change The technique of ultrasonic echoscopy is used in medical diagnosis to obtain information about the anatomy of patients. The application of this technique is now widely investigated and is described, for example, by D. E. Robinson in Proceedings of the Institution of Radio and Electronics Engineers Austrialia, Vol. 31, No. 11, pages 385-392, November, 1970: "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, didney, liver and heart, these being arear of soft tissue with little bone and air. In general, the technique is considered to complement other techniques to provide a more complete picture of the patient's condition, However, particularly in pregnancies, ultrasonic echoscopy may be useful in place of X-ray where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross-section as previously described.

The present invention has for its object the optimising of the amount of usable information which can be transferred from an input signal applied to a processing system to a display device viewed by an interpreter.

The invention provides, in one aspect an echoscope including in series:

a transducer to receive echoes of an earlier transmitted non-electrical signal and to convert the received echoes into representative electrical signals;

a time gain compensation amplifier to amplify said electrical signals in dependence upon the relative delay time between transmission of the original non-electrical signal and receipt of the echo; and compression means to limit the amplitude range of the signals received from the time gain compensation amplifier;

the improvement wherein said compression means comprises:

a plurality of amplitude limiting means connected in series to pass signals applied to the first such means while compressing the amplitudes of those applied signals which exceed a characteristic value for each such means, the electrical parameters of each amplitude limiting means being selected such that the characteristic applied signal amplitude values for the amplitude limiting means are successively smaller, an adder connected to produce an adder output signal being the sum of adjustable proportions of the output signals from at least the first and last of said series connected amplitude limiting means; and a switch for selectively producing a final output signal comprising either an output from said last amplitude limiting means or said output signal.

In a second aspect, the invention provides an echoscope including in series;

a transducer to receive echoes of an earlier transmitted non-electrical signal and to convert the received echoes into representative electrical signals;

a time gain compensation amplifier to amplify said electrical signals in dependence upon the relative delay time between transmission of the original non-electrical signal and receipt of the echo;

compression means to limit the amplitude range of the signals received from the time gain compensation amplifier; and an output signal processor to modify the signal received from the compression means for presentation to a display;

the improvement wherein said output signal processor comprises:

filter means to produce a first signal being an envelope of a rectified signal representative of a signal train applied to the filter means;

derivating means to produce a second signal being a derivative with respect to time of at least a leading portion of an envelope of a rectified signal representative of said signal train; and adding means to produce a further signal being a summation of said first and second signals.

The invention will now be described in detail by way of example with reference to the accompanying drawings, in which.

Figure 1:
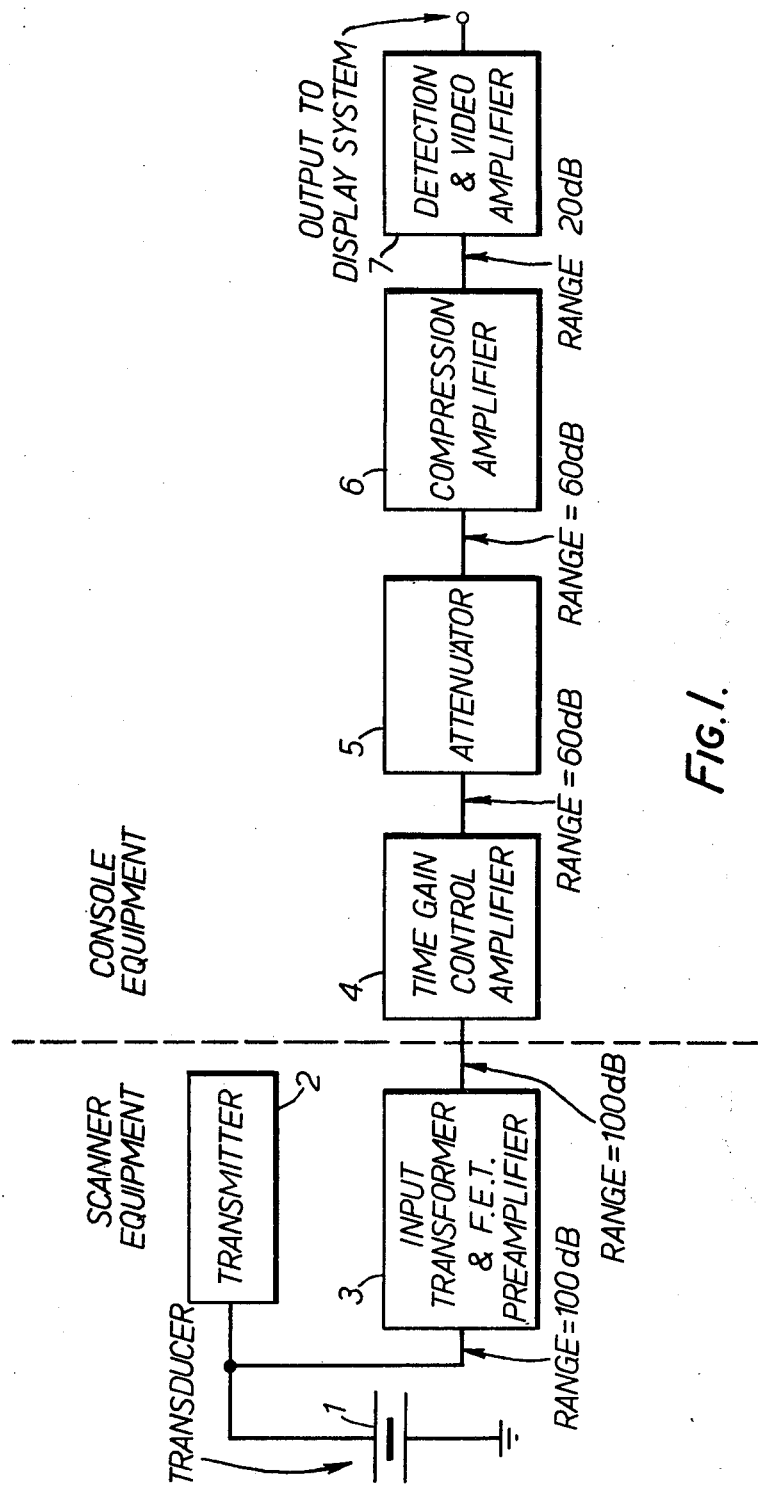
FIG. 1 is a basic block diagram of the signal electronics of an ultrasonic echoscope.

An outline of the processing system for an ultrasonic echoscope is shown in FIG. 1. The transducer 1 is energised by a short electrical pulse from a transmitter 2 and converts this pulse to a sound pulse which travels into the tissue being examined. At any impedance discontinuities within the tissue echoes are reflected back to the transducer and reconverted to a representative electrical signal. The characteristics of these echoes are that they are generally of quite low level (a maximum of 100 mV) and have a wide range of amplitudes of the order of 100,000;1 or 100 decibels (db). One of the objects of the signal processing stages of the echoscope is to reduce this wide range to the order of 10:1 or 20 db, which can be handled by the display device, which may be a cathode ray tube, film display, T.V. or hard copy readout.

An input transformer and preamplifier 3 are used to amplify the incoming signals or echoes to a level which can be handled by the signal processing states. A Time Gain Compensation (TGC) amplifier 4 varies its gain depending on the arrival time of echoes in order to compensate for the attenuation of ultrasound in tissue so that echoes from deeper within the tissue which have experienced more attenuation are amplified to a greater degree. This reduces the range of echo amplitudes to the order of 60 db. The attenuator 5 is simply used to control the level of echoes which will be displayed.

A compression amplifier 6 is used to compress this dynamic range of 60 db down to 20 db which can be handled by the display device. In accordance with the invention, this compression characteristic is not a simple logarithmic curve but has a particular characteristic which needs to be varied for particular organs being examined and for particular types of scan. The circuit according to the first aspect of the invention has been developed to give these particular characteristics and to allow an easy changeover from one type to another.

An output signal processor in the form of a detection and video amplifier 7 is used to give a unipolar signal suitable for the brightness modulation of the display system and to give optimum display of this detected information. The circuit according to the second aspect of the invention may be used at this point to further optimise the display and is particularly useful when a point is scanned from a number of different directions and the echoes are integrated up to give the final brightness representing the point on the display screen.

Figure 2:
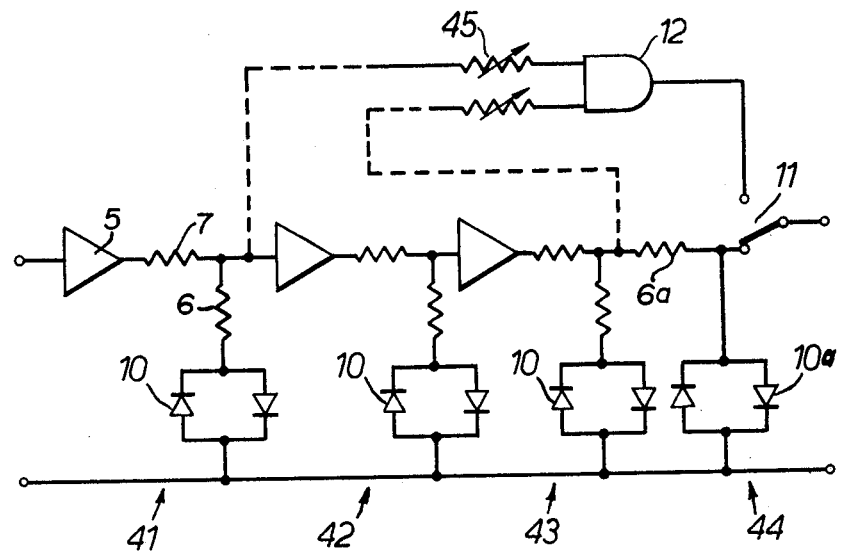
FIG. 2 is a circuit diagram of a compression amplifier for the echoscope and being arranged in accordance with the first aspect of the invention.
Figure 3:
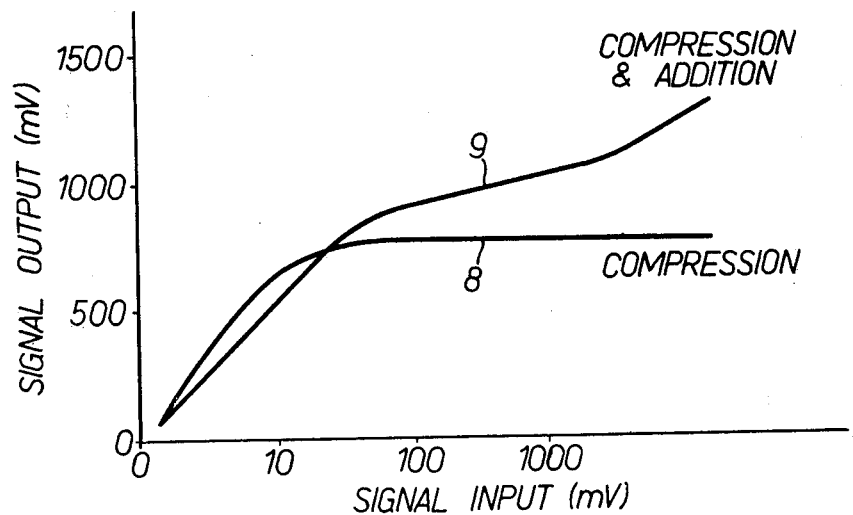
FIG. 3 shows the characteristic curves of the compression amplifier of FIG. 2.

Reverting to the compression amplifier 6, two of the particular compression characteristics which are realized, in accordance with the invention, to be of value, for reasons to be outlined, are depicted in FIG. 3, while appropriate circuitry for achieving these characteristics is detailed in FIG. 2. The circuit includes three series, arranged amplitude limiting stages 41,42,43 which pass applied pulses while compressing successively smaller signals of those presented at the input to the first stage. Each succeeding stage thus further reduces the range of pulse echo amplitudes.

Each of the stages 41,42,43 includes a series connected amplifying device 5, resistors 6 and 7 and a diode network 10 which attenuates the output of the stage when the voltage level out of the stage rises above the conduction level of the diodes. The electrical parameters of the circuit are chosen such that the stages 41,42,43 respectively compress the amplitudes of those signals applied to stage 41 which exceed a characteristic value for each stage, these values being smaller for each successive stage.

Figure 4:
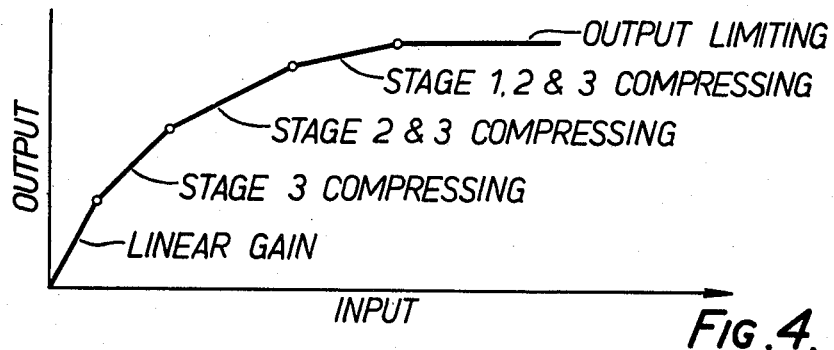
FIG. 4 shows the build up of a compression characteristic.

Thus, a large signal applied to the first stage is compressed in all 3 stages while smaller initial signals are compressed in only the third, or the third and second stages. When a low level signal, say below 10 mV, is fed into the amplifier it will typically pass through the first two or three stages without causing the diode pairs to conduct whereas larger signals will cause the diodes to conduct at an earlier stage in the amplifier. As each diode pair is made to conduct it effectively reduces the gain of that particular stage and hence the piecewise amplitude versus input amplitude compression characteristic of the form depicted in FIG. 4 and at 8 in FIG. 3 is generated.

The circuit of FIG. 2 further includes an adder 12 connected to produce an adder output signal being the sum of adjustable proportions of the output signals from at least the first and last of the amplitude limiting stages. Variation of the relative proportional contributions to the summed signal of the respective output signals is effected by control means 45. Additional control over the form of the characteristic may be gained by providing for resistors 6 to be variable. The circuit is completed by an output clipping resistor and diode arrangement 44, including a diode pair 10a, connected across the diode network 10 of amplitude limiting stage 43, and by a switch 11 for selectively producing a final output signal comprising either the output of stage 43 or the output of adder 12.

To obtain a characteristic as shown in curve 9 (FIG. 3) signal from the first gain stage 41 which has undergone very little compression is added to the output of the final stage 43 in adder 12. With appropriate choice of circuit parameters, large signals will also cause the diode pair 10a of stage 44 to conduct and a low value of the resistor 6a feeding these diodes will result in output clipping on the signal after stage 43. Hence it is possible for relatively large signals to appear at the output of the first stage 4 and be fed to adder 12, whereas these same signals when appearing at the output of the third stage 43 and also fed to adder 12 will be of a lower level due to the clipping effects of the diode pair 10a. In this way it is possible for the characteristic curve 9 to exhibit the illustrated upward swing at high levels.

Figure 5:
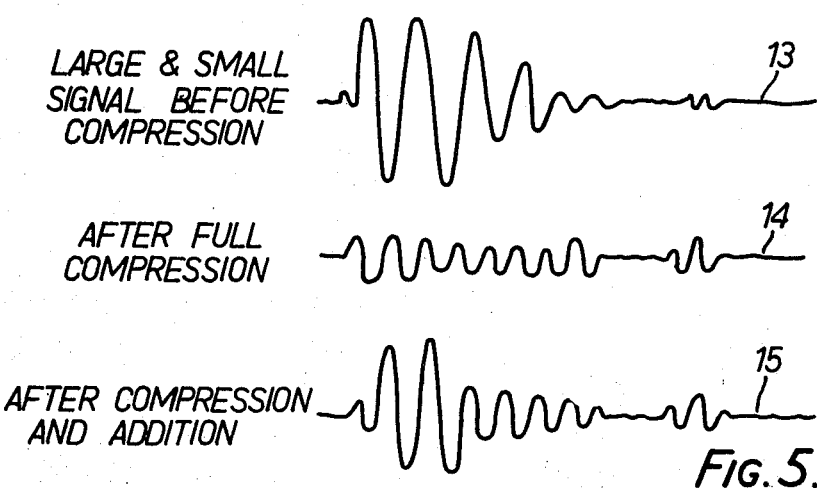
FIG. 5 shows typical waveforms in relation to the circuit of FIG. 2.

An example of the effect of compression and addition on echo waveforms presented to the circuit of FIG. 2 is demonstrated in FIG. 5. A large echo signal 13 after full three-stage compression becomes a very long waveform 14 with little variation in amplitude. This is improved by the addition of output signal from the first amplitude limiting stage 41 which has undergone much less compression, to give the final signal 15. It will be seen that the overall output has an improved shape for the large echoes while maintaining the level of the smaller echoes.

In a practical circuit according to FIG. 2, capable of exhibiting the characteristics curves 8 and 9 of FIG. 3, the amplifier gain levels are set such that the amplifier 5 of stage 41 has a high gain of the order of $30\times$ and the two succeeding amplifiers have lower gains of the order of $4\times$. Each of the resistors 6,7 is of the order of 500 ohms. The resistor 6a leading to the clipping diode pair 10a is of a low value of the order of 10 ohms. The conduction level of the three diode pairs 10 is typically of the order of 0.3 V and the conduction level for the diode pair 10a is of the order of 0.7 V. The characteristic curves 8 and 9 shown in FIG. 3 have been found to be of value for different echoscope applications. For example, in scanning a fetus within the pregnant uterus it is important that the large outline echoes obtained from such areas as the fetal skull and fetal spine are compressed and limited to within the dynamic range of the display system and hence curve no. 8 of FIG. 3 is suitable. In scanning normal liver it is important to show the internal texture and hence curve 9 of FIG. 3 is used with the internal textural echoes occurring on the flattened portion of the curve. The increase in output for very high level echoes is used in this case to highlight boundaries between other organs such as the liver and kidney or the liver and pancreas.

Figure 6:
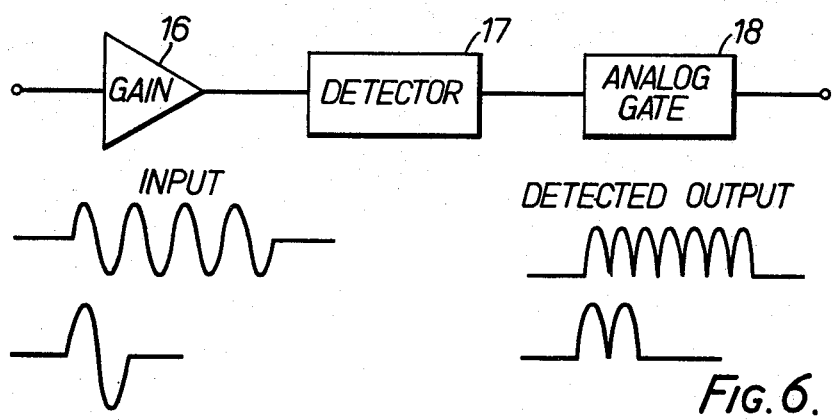
FIG. 6 is a block diagram of a generalized detection and video amplifier for the echoscope of FIG. 1.
Figure 7:
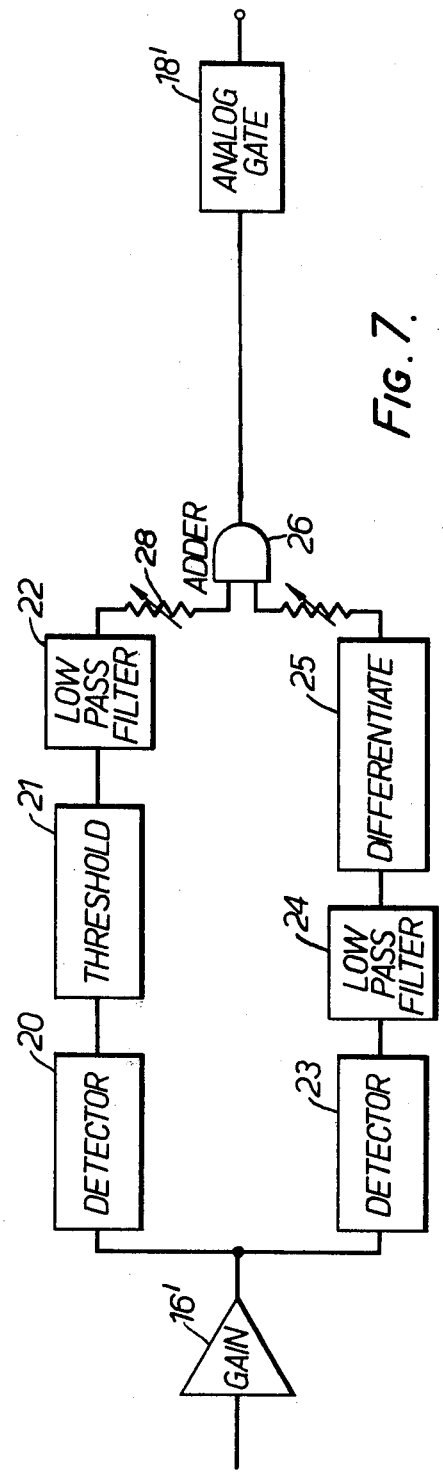
FIG. 7 is a circuit diagram corresponding to FIG. 6 but embodying the second aspect of the invention.

The standard detector and video amplifier for an echoscope is outlined in FIG. 6 and consists of simply a gain stage 16, a detector 17 and an analogue gate 18: this has been found to be satisfactory when a point is scanned from only one direction. In its second aspect, the invention provides a circuit capable of improving the display of points which have been scanned from many directions. The circuit is shown in FIG. 7 and broadly entails the passage of an applied signal through two processing chains prior to recombination.

The signal is split after the gain stage 16' and in the upper path is detected or rectified at 20, then passed through a low pass filter 22 to give the envelope of the waveform.

Figure 8:
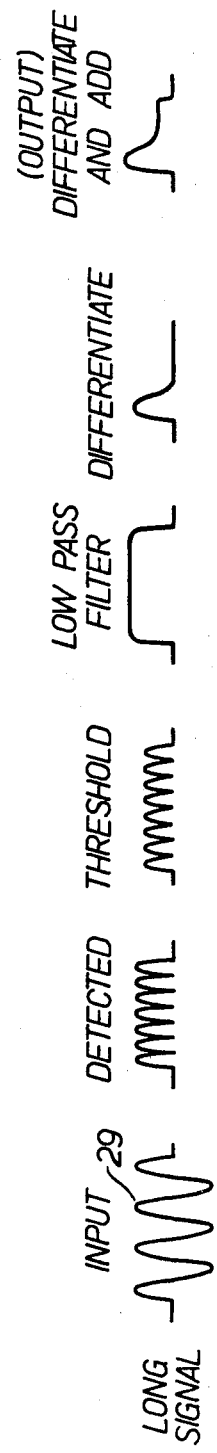
FIG. 8 shows typical waveforms in relation to the circuit of FIG. 7.

This detector is set up with a degree of threshold 21 so that very small signals do not pass the detector. The lower path is similar except that the envelope of the detected signal is then differentiated at 25 which has the effect of emphasising the leading edge of the echo waveform. Note that this process of differentiating has little effect on short echoes 30 (FIG. 8) but a marked effect on long ones 29. These two signal paths are then combined in the adder 26 such that most of the contribution is from the upper path (undifferentiated) with only a small amount of differentiated signal being added. Controls 28 are provided for determining the relative combinations of the two paths to the combined signal. This combined signal is then passed through the analogue gate 18' to the display system. The analogue gate is used to pass only those echoes from the area being scanned and to shut off at other times to eliminate spurious and artifact echoes and as such is not unique to this circuit.

In summary, the circuit of FIG. 2 has the advantage that a wide range of compression characteristics can be achieved by the compression and addition characteristic which can not be easily achieved with a simple compression circuit alone.

The circuit of FIG. 7 has the advantage that short echoes maintain their amplitude and pulse characteristics whereas longer echoes have their leading edge emphasized so that their displayed resolution is improved. This can be achieved by simply differentiating the signal but this has the disadvantage of losing the amplitude information of the signal. This circuit by using two signal paths and achieving a differentiate and addition process, retains amplitude information in the final signal. Also it allows the amount of differentiation to be easily varied by changing the ratio of signal added from each path to the final output.

We claim:

1. In an echoscope including in series:
   a transducer to receive echoes of an earlier transmitted non-electrical signal and to convert the received echoes into representative electrical signals;
   a time gain compensation amplifier to amplify said electrical signals in dependence upon the relative delay time between transmission of the original non-electrical signal and receipt of the echo; and
   compression means to limit the amplitude range of the signals received from the time gain compensation amplifier;
   the improvement wherein said compression means comprises:
   a plurality of amplitude limiting means connected in series to pass signals applied to the first such means while compressing the amplitudes of those applied signals which exceed a characteristic value for each such means, the electrical parameters of each amplitude limiting means being selected such that the characteristic applied signal amplitude values for the amplitude limiting means are successively smaller,
   an adder connected to produce an adder output signal being the sum of adjustable proportions of the output signals from at least the first and last of said series connected amplitude limiting means; and
   a switch for selectively producing a final output signal comprising either an output from said last amplitude limiting means or said adder output signal.

2. The improved echoscope according to claim 1 wherein each amplitude limiting means includes a respective arrangement of diodes for attenuating the signals passed by that means when their voltage level exceeds the conduction level of the diodes.

3. The improved echoscope according to claim 2 wherein each amplitude limiting means includes an amplifying device and a resistor in series with the respective arrangement of diodes, each successive amplitude limiting means being connected across the diode arrangement of the preceding amplitude limiting means.

4. The improved echoscope according to claim 3 wherein the conduction levels of said diode arrangements are substantially equal, the values of said resistors are substantially equal, and the gain of the last amplifier devices is smaller than that of the first.

5. The improved echoscope according to claim 3 or 4 further comprising a clipping resistor and diode arrangement connected in parallel with the diode arrangement of the last amplitude limiting means.

* * * * *